United States Patent [19]
Habraken et al.

[11] Patent Number: 5,828,221
[45] Date of Patent: Oct. 27, 1998

[54] ELECTROMAGNETIC OBJECT DETECTOR FOR A MEDICAL DIAGNOSTIC APPARATUS

[75] Inventors: Wilhelmus J. P. Habraken; Antonius H. M. Blom; Ronald J. Asjes, all of Eindhoven, Netherlands

[73] Assignee: U.S. Philips Corporation, New York, N.Y.

[21] Appl. No.: 758,653

[22] Filed: Dec. 2, 1996

[30] Foreign Application Priority Data

Nov. 30, 1995 [EP] European Pat. Off. .............. 95203299

[51] Int. Cl.$^6$ .................................................. G01R 27/26
[52] U.S. Cl. .......................... 324/662; 324/601; 324/671; 324/687
[58] Field of Search .................................... 324/601, 662, 324/661, 671, 672, 679, 687

[56] References Cited

U.S. PATENT DOCUMENTS

| | | | |
|---|---|---|---|
| 4,054,833 | 10/1977 | Briefer | 324/679 |
| 5,194,819 | 3/1993 | Briefer | 324/662 |
| 5,281,921 | 1/1994 | Novak | 324/662 |
| 5,557,267 | 9/1996 | Poduje | 324/601 |
| 5,583,443 | 12/1996 | McMurthy | 324/601 |

FOREIGN PATENT DOCUMENTS 4126168  2/1992  Germany.

Primary Examiner—Josie Ballato
Assistant Examiner—Jose M. Solis
Attorney, Agent, or Firm—Dwight H. Renfrew, Jr.

[57] ABSTRACT

An apparatus for medical diagnosis and/or therapy, includes an electromagnetic obstacle sensor. Due to variations of the ambient temperature and humidity and/or due to the hanging of, for example a cloth around the sensors (16,18), drift of the zero point of the control may occur, so that the approaching of an obstacle by a movable part (6) of the apparatus could be incorrectly interpreted by the apparatus. In order to compensate for such drift there is provided a control unit (25) for automatically controlling the output signal $V_o$ of the receiver (27) back to the zero value in the absence of an object in the vicinity of the movable part (6). This control preferably takes place at a comparatively high speed when a cloth or moisture is moved into the vicinity of the sensors, and at a comparatively low speed upon removal of the cloth or the moisture. As a result, the nature of the movement of the drive is maintained for some time after the displacement of the movable part, thus contributing to the ease of operation of the apparatus.

17 Claims, 2 Drawing Sheets

ELECTROMAGNETIC OBJECT DETECTOR FOR A MEDICAL DIAGNOSTIC APPARATUS

BACKGROUND OF THE INVENTION

1. Field of the Invention

The invention relates to an apparatus for medical diagnosis and/or therapy, including a detection device for electromagnetic detection of the presence of an object in the vicinity of a movable part of the apparatus, which detection device includes a signal source for producing an electric signal, a transmitter unit which is connected to the signal source in order to produce in the vicinity thereof an electromagnetic field corresponding to the electric signal, a detection unit which is arranged in the vicinity of the transmitter unit in order to detect an electromagnetic field in the vicinity thereof, and a receiver which is arranged to receive on an input an input signal which corresponds to the electromagnetic field in the vicinity of the detection unit and to produce an output signal corresponding to the input signal.

2. Description of the Related Art

An apparatus of this kind is known from the German published Patent Application DE 41 26 168.

An apparatus for medical diagnosis and/or therapy may include a radiation transmitter and a radiation receiver. An example in this respect is a medical X-ray apparatus provided with an X-ray source and an X-ray receiver which is usually called an image intensifier. These two elements are arranged at some distance from one another, the patient to be examined or treated being a between the X-ray source and the image intensifier. The X-ray source and the image intensifier are positioned relative to the body of the patient in such a manner that an image can be formed of the desired region of the body (the "object"). The orientation and position of such apparatus can often be adjusted by means of a motor drive. Generally speaking, in the context of the present invention an object is to be understood to mean the body of a patient to be examined or another object to be examined, the body or a part of the body of a person operating the apparatus, parts of the apparatus itself (for example, the patient table) or of neighboring apparatus, or other obstacles which could move into the path of movement of the parts of the apparatus.

Many of such apparatus comprise a so-called C-arm, i.e. a semi-circular support which is rotatable in its own plane via a guide or trackway (i.e. about an axis extending perpendicularly to the plane in which the C-arm is situated), which own plane is rotatable about an axis situated in said plane. Moreover, often a number of other possibilities for displacement are also provided.

During use of the apparatus it is important that a movable part, for example the image intensifier, closely approaches the object to be examined in order to achieve the desired clarity of the image. The image intensifier has a comparatively large front face for receiving the X-rays and each point on this front face or on its circumference can come into contact with the object to be examined. Such a collision can occur in any direction of movement of the image intensifier. This is undesirable and, therefore, such an apparatus comprises a detection device for detecting the presence of an object in the vicinity of the movable part of the apparatus.

It is important to provide such a detection device notably in the case of motor-driven apparatus. When an object is detected within a given small distance from the movable part of the apparatus, the movement of (that part of) the apparatus can be stopped so as to avoid a collision. The cited Patent Application DE 41 26 168 shows a medical X-ray apparatus which includes an electromagnetic collision sensor enabling detection of the presence of an object within a given small distance from the movable part of the apparatus. This apparatus includes a signal source for producing an electric signal in the form of a fixed voltage. This voltage is applied to a transmitter unit in the form of a metal foil. In the vicinity of the metal foil, but electrically insulated therefrom, there is arranged another metal foil which acts as a detection unit. Between these two metal foils a signal can be measured which corresponds to the electromagnetic field strength in the vicinity of the collision sensor. This signal is further processed by means of a receiver which consists of a number of amplifiers and produces an output signal corresponding to the field strength.

During use of such an apparatus it is desirable to distinguish the situation in which a moving part of the apparatus threatens to collide with an object from a situation in which an object is arranged more or less permanently in the vicinity of the moving part. This may occur if a sterile cloth is fitted around the moving part (for example, the image intensifier) so that the electromagnetic field in the vicinity of the detection unit is influenced. This holds even more so if said sterile cloth becomes wet during use or if moisture can directly reach the image intensifier during use of the apparatus, as may occur in many practical situations in medical apparatus. The presence of the cloth and/or the wetting thereof is not to be interpreted as the presence of an obstacle by the detection device, because otherwise the apparatus would continuously undertake control actions in order to avoid an (imaginary) collision.

SUMMARY OF THE INVENTION

It is an object of the invention to provide an apparatus of the kind set forth in which said changes in the vicinity of the detection unit do not have a disturbing effect on the behaviour and the operation of the apparatus. To this end, the apparatus in accordance with the invention is characterized in that the detection device includes a control unit for automatically adjusting the output signal of the receiver to a predetermined nominal zero value in the absence of an object in the vicinity of the movable part of the apparatus.

The invention is based on the following idea. When a cloth is fitted around the image intensifier, or when wetting takes place, the receiver connected to the detection unit will produce a signal other than when an object is approached in the vicinity of the moving apparatus part. This is due to the fact that objects in the vicinity have a connection to ground (either a conductive connection or, as is often the case with patients, a strong capacitive coupling), whereas said cloth, wetted or not, is not connected to ground or has at least a negligibly small capacitive coupling to ground. As a result, the control unit can distinguish the two situations and adjust the output signal of the receiver to a predetermined nominal zero value in the absence of an object in the vicinity of the movable part of the apparatus (i.e. without intervention of the attending staff). In the context of the present invention a nominal zero value is to be understood to mean the value of the output signal of the receiver in the absence of an obstacle and in the absence of disturbing cloths or moisture in the direct vicinity of the detection unit. When a cloth is arranged on the detection unit in the absence of an obstacle, the value of the output voltage will initially exhibit a deviation. The value then occurring may be referred to as a zero value, because no obstacle is present. The control unit then restores the output value to the original value, the nominal zero value, which also existed in the absence of an obstacle and the cloth.

In an embodiment of the invention the control unit of the apparatus includes a controllable transfer unit which is arranged for the controllable transfer of the output signal of the signal source to an input of the receiver in order to control the output signal of the receiver to the nominal zero value. Because the control unit can subtract the output signal of the signal source more or less from the input signal corresponding to the electromagnetic field in the vicinity of the detection unit, control to the nominal zero value of the output of the receiver is facilitated and made independent of the frequency or the waveform of the signal source.

In another embodiment of the invention, the control unit of the apparatus includes an adjusting unit which is arranged to control the transfer of the transfer unit in dependence on the output signal of the receiver, said adjusting unit being arranged to adjust the output signal to the nominal zero value with a first time constant if the output signal is in a first range, and to adjust the output signal to the nominal zero value with a second time constant if the output signal is in a second range.

The following advantages are achieved by means of the described steps. As has already been described, when a cloth is fitted or in the case of wetting, the receiver will produce a signal (the first case in which the output signal is in a first range) other than when an object is approached (the second case in which the output signal is in a second range). In the first case it is certain that there is no risk of collision (because the first signal range occurs when a cloth is fitted, upon wetting, or upon moving away from an obstacle), so that adjustment to the nominal zero value of the output signal can take place quickly (i.e. with the first time constant). In that case the disturbance caused by the deviation from the nominal zero value is only brief. In the second case the occurrence of the second signal range may be due to the approaching of an obstacle, or to the removal of the cloth, or to the drying of the moisture. The control system of the apparatus knows the situation of approaching an obstacle, because the movable part is driven so that this situation can be distinguished from the other circumstances. However, after the approaching of an object it is desirable that the movement behavior of the apparatus remains the same for some time (for example, for one half minute) as during the movement. This is desirable because after adjustment of (for example) the image intensifier, the adjustment is checked on a display screen after which, if necessary, a correction takes place. During this correction no movement behaviour of the apparatus other than that immediately before the correction is desired: slow movement of the image intensifier during the first approach may not be suddenly replaced by fast movement during the correction. To this end, adjustment of the output signal to the nominal zero value should take place comparatively slowly (i.e. with the second time constant).

In a further embodiment of the apparatus in accordance with the invention, the detection device for electromagnetic detection is constructed as a device for capacitive detection. The transmitter unit and the detection unit are then both constructed as an electrode which can readily be given a large number of shapes, thus facilitating the manufacture of the apparatus.

In a further embodiment of the apparatus in accordance with the invention, the detection electrode is virtually grounded, thus stimulating stable behaviour of this electrode relative to external electric fields. Ground potential is to be understood to mean herein the potential of the remainder of the apparatus.

In another embodiment of the apparatus in accordance with the invention, virtual grounding is realized in that the detection electrode is connected to a first input of an operational amplifier which is connected to the output via a feedback chain, a second input of said amplifier being grounded.

BRIEF DESCRIPTION OF THE DRAWINGS

These and other aspects of the invention will become apparent from and elucidated hereinafter, by way of example, with reference to the drawings. Therein.

DETAILED DESCRIPTION OF THE PREFERRED EMBODIMENTS

Figure 1:
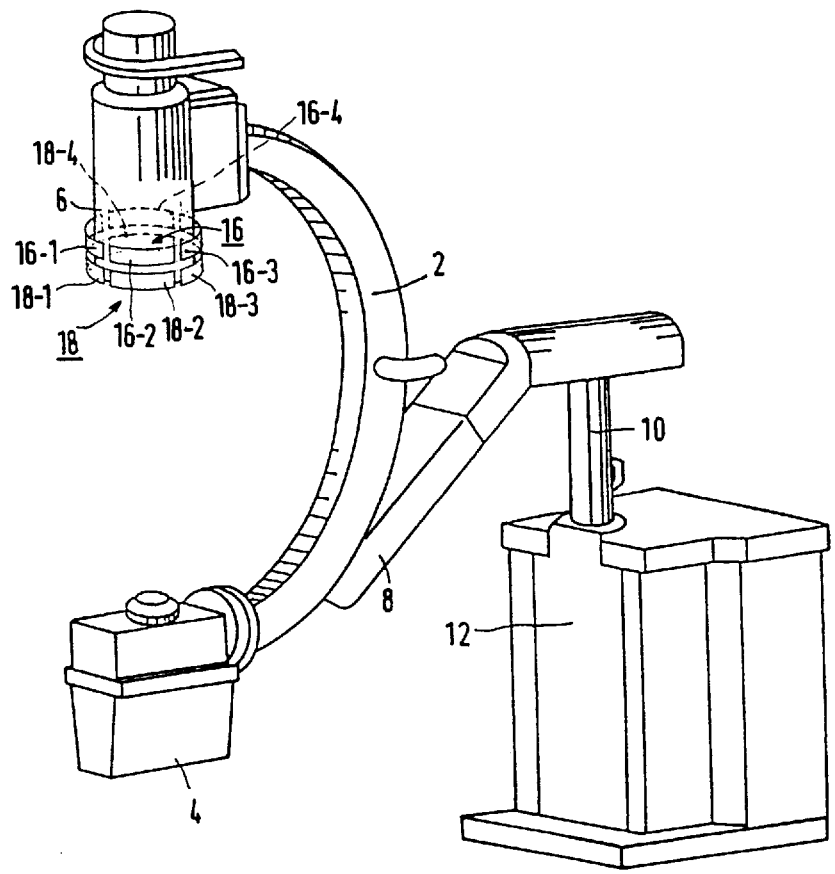
FIG. 1 is a general view of a medical X-ray apparatus in which electromagnetic detection of the presence of an obstacle can be used.

FIG. 1 is a general view of a medical diagnostic and/or therapy apparatus in the form of an X-ray apparatus. The X-ray apparatus is constructed so as to include a carrier 2 on which an X-ray source 4 and an X-ray image intensifier 6 are mounted. The carrier is shaped as an arc of circle so that it can be rotated about an axis extending perpendicularly to the plane of the arc of circle by means of a guide or trackway 8. This kind of carrier is known as a C-arm; generally speaking, they are also rotatable about an axis extending in the plane of the arc of circle. The rotation mechanism for the latter movement is not shown in the figure. The assembly formed by the carrier 2 and the guide 8 is also rotatable about a shaft 10. This shaft is mounted on a stand 12 which may be constructed so as to be mobile, if desired. The X-ray source 4 and the X-ray detector 6 preferably are also displaceable relative to the carrier 2. For easy displacement of these components there is provided a motor drive which is not shown in the Figure. The object to be examined, being the body of a patient to be examined or treated in the present example, is arranged on a table (not shown) which is positioned between the image intensifier 6 and the X-ray source 4. As a result of the described possibilities of movement of the C-arm 2, the image intensifier 6 and the X-ray source 4, these components can be positioned in all desirable directions relative to the patient and images can be formed of all desired slices.

Because of their mobility, the movable parts, such as the image intensifier 6 and the X-ray source 4, can readily come into contact with the body of the patient to be examined or with other obstacles. This is undesirable and, therefore, the image intensifier of the present embodiment includes a detection device for detecting the presence of an object in the vicinity of the movable part of the apparatus. The detection device includes a transmitter unit 16 and a detection unit 18. The transmitter unit 16 is formed as an annular electrode 16 which is arranged around the end of the image intensifier 6 in order to produce an electromagnetic field in the vicinity thereof. The detection unit 18 is formed as an annular electrode 18 which is arranged around the end of the image intensifier 6 and in the vicinity of the electrode 16 in order to detect the electromagnetic field produced by the electrode 16 and distorted by the object to be detected. The annular electrodes 16 and 18 can be subdivided into ring sectors 16-1, 16-2, 16-3, 16-4 and 18-1, 18-2, 18-3, 18-4, respectively, in order to achieve directional sensitivity. The production of signals by the electrode 16 and the detection of signals by the electrode 18 will be described with reference to FIG. 2.

Figure 2:
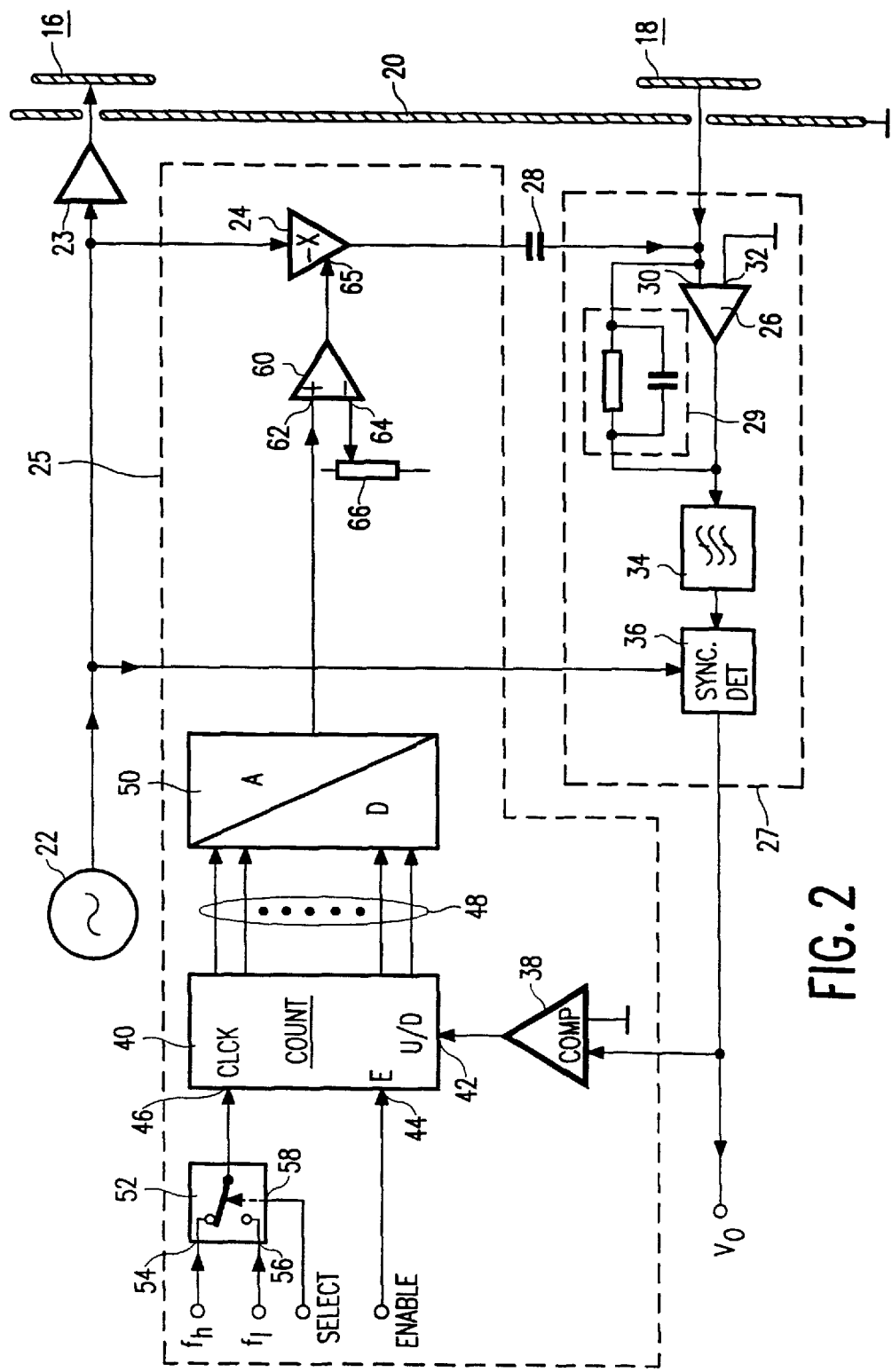
FIG. 2 shows an electrical diagram of a detection device in accordance with the invention.

FIG. 2 shows an electrical diagram of the detection device in accordance with the invention. A signal source 22 produces a sinusoidal electric signal which has an amplitude of the order of magnitude of 5 V and a frequency of the order of magnitude of 100 kHz. The signal source 22 is connected, via a buffer amplifier 23, to the electrode 1 acts, in this embodiment, as a transmitter unit for producing an electromagnetic field, corresponding to the electric signal, in the vicinity of the electrode 16. The electrode 16 is situated outside the housing 20 of the image intensifier 6. The housing 20 is connected to a point carrying a fixed voltage, referred to as system ground. The output signal of the signal source 22 is also applied to the signal input of a controllable transfer unit in the form of a variable amplifier 24. The amplifier 24 also reverses the sign of the signal applied thereto.

The output signal of the amplifier 24 is applied, via a coupling capacitor 28, to the inverting input 30 of the operational amplifier 26. This amplifier is an operational amplifier which is fed back via a feedback chain 29 consisting of a parallel connection of a resistor of 20 MΩ and a capacitor of 15 pF. The input 30 is also connected to the electrode 18 which acts, in the present embodiment, as a detection unit for the detection of an electromagnetic field in its vicinity. The electrode 18 is situated outside the housing 20 of the image intensifier 6.

The non-inverting input 32 of the amplifier 26 is connected to system ground. The output signal of the amplifier 26 is applied, via a bandpass filter 34, to a synchronous detector 36; another input of this detector receives the output signal of the signal source 22. The output of the synchronous detector 36 is connected to an input of a comparator 38 whose other input is connected to system ground. The output of this comparator is connected to an Up/Down input (U/D) 40 of a counter 42. The operational amplifier 26, the bandpass filter 34 and the synchronous detector 36 together constitute the receiver 27 which is connected so as to receive, on an input 30, an input signal corresponding to the electromagnetic field in the vicinity of the detection unit 18, and to produce an output signal $V_o$ corresponding to the input signal.

The counter 40 also includes an enable input (E) 44, a clock input (CLCK) 46 and a number of parallel output conductors 48. The output value of the counter 40 is reproduced on the output conductors 48 in digital form. These output conductors are connected to the input conductors of a digital-to-analog converter 50. A selection circuit 52 for applying an input signal having a comparatively high frequency $f_H$ or a comparatively low frequency $f_L$, as desired, is connected to the clock input 46 of the counter 40. The selection between these two signals is made by means of a selection signal "SELECT" which is applied to the selection input 58.

The D/A converter 50 converts the digital output value from the counter 40 into an analog value which is applied to the non-inverting input 62 of the operational amplifier 60. The inverting input 64 of the operational amplifier 60 is connected to a zero point setting which is symbolically represented by an adjusting potentiometer 66. The output signal of the operational amplifier 60 is applied as a control signal to the control input 65 of the variable amplifier 24.

The comparator 38, the counter 40, the selection circuit 52, the D/A converter 50, the amplifier 60 and the amplifier 24 together constitute the control unit (25) for automatically adjusting the output signal $V_o$ of the receiver 27 to a predetermined nominal zero value in the absence of an object in the vicinity of the movable part of the apparatus.

The signal produced by the signal source 22 is applied to the electrode 16 via the buffer amplifier 23. It is assumed that initially no object is present in the vicinity of this electrode. A capacitive coupling exists between the electrodes 16 and 18, so that the electric field produced by the electrode 16 induces an electric signal in the electrode 18. This signal is amplified by the amplifier 26 and undesirable frequency components are removed therefrom by the bandpass filter 34. This electric signal is converted into a direct voltage signal $V_o$ in the synchronous detector 36, the value of said signal being a measure of the amplitude of its input signal. The output signal of the synchronous detector 36 constitutes the signal indicating whether an obstacle is situated so close to the image intensifier that a control operation is necessary. This direct current signal is also used to control the movement of the movable parts of the apparatus. This method of control does not form part of the invention and, therefore, will not be elaborated upon herein. In the comparator 38 the direct current signal $V_o$ is compared with the voltage zero (system ground) and the comparator produces a positive or a negative signal, depending on the sign of $V_o$.

When a grounded object (for example, a patient to be examined by means of the X-ray apparatus) approaches the electrodes 16 and 18, the voltage on the input, and hence also $V_o$, increases due to the capacitive coupling between the electrodes. As a result, the output voltage of the comparator 18 will become or remain positive, so that the counter 40 is driven in such a manner, via the input 42, that it counts up. It is assumed that the counter initially was in the position zero; subsequently, it starts to count in response to a signal on the enable input (E) 44. Depending on the selection signal SELECT to be described hereinafter, counting up takes place with a high counting frequency $f_H$ or with a low counting frequency $f_L$. Consequently, a gradually increasing digital value appears on the output 48 of the counter 40, causing a gradually increasing analog value to appear on the output of the D/A converter 50. This value is applied to the non-inverting input 62 of the amplifier 60.

The inverting input 64 of the amplifier 60 is connected to a zero point setting which is symbolically represented by an adjusting potentiometer 66. The zero point setting is used for a first, coarse adjustment of the zero point of the output voltage $V_o$ upon installation of the apparatus. Further adjustment of the zero point of the output voltage $V_o$ takes place automatically in accordance with the invention. The output value of the D/A converter 50 is transferred from the amplifier 60 to the control input 65 of the amplifier 24, thus controlling the amplification of the output signal of the signal source 22. The latter signal is multiplied by a negative value and added to the input signal on the input 30 of the receiver 27. Due to the addition of this inverted signal, the signal applied to the input 30 of the amplifier 26 is smaller than the signal originating from the electrode 18. For as long as the output voltage $V_o$ is positive, the counter is incremented and hence the inverted signal to be added on the input 30 also increases. This process continues until the output voltage $V_o$ has become smaller than zero. In the case of a negative value of the output voltage $V_o$, the reverse of the described process occurs; consequently, in the case of a constant signal from the electrode 18 the count starts to vary around zero with a variation of the least-significant bit so that the output voltage remains substantially equal to zero.

The described situation occurs when the image intensifier of the apparatus is not driven; the signal on the enable input 44 enables the counter to execute counting operations in that situation. When the image intensifier is driven, such a signal is applied to the enable input 44 by the control logic of the apparatus (not shown in the Figure) that the counter does not perform a counting operation. Consequently, in this situation the output voltage $V_o$ can vary freely so that it can indicate whether an obstacle is present in the vicinity of the electrodes 16 and 18, on the basis thereof the control logic of the apparatus can decide to undertake control actions.

It is assumed that a cloth is hung over the image intensifier or that the image intensifier or the cloth is wetted. Because in that case the object is not grounded, the output voltage $V_o$ will become negative. On the basis of this negative value the control logic of the apparatus can decide directly that this change cannot be attributed to an object moving away (because no drive action takes place, as is known to the logic), so that fast control (i.e. with a small time constant) of the output voltage $V_o$ back to zero is possible. The same will happen when the output voltage varies in the negative sense due to causes other than the hanging of a cloth or wetting (for example, due to a change of temperature or the relative humidity of the environment or drift in the electronic circuitry of the control system). Fast control then takes place in that the control logic outputs such a SELECT signal that the high-frequency counting signal $f_H$ is applied to the clock input 46 of the counter 40.

A variation of the output voltage in the positive sense may be due to drying of previously applied moisture, removal of a cloth, or the approaching of an obstacle. The latter situation is known to the control logic; the signal on the input 44 then inhibits counting by the counter. In the other cases the control back to the nominal zero value of the output signal takes place comparatively slowly (i.e. with the second time constant). Slow control is desirable for the following reason. After the approaching of an object, it is desirable that the movement behaviour of the apparatus remains the same as during the movement for some time (for example, half a minute). This is desirable because after the adjustment of (for example) the image intensifier, the adjustment must be checked on a display screen, after which correction is performed, if necessary. During this correction motional behaviour of the apparatus other than just before correction is not desirable: slow motion of the image intensifier during the first approach may not be suddenly replaced by a fast movement upon correction. Therefore, controlling the output signal back to the nominal zero value should take place comparatively slowly (i.e. with the second time instant). Slow control takes place in that the control logic outputs such a SELECT signal that the low-frequency counting signal $f_L$ is applied to the clock input 46 of the counter 40.

We claim:

1. An apparatus for medical diagnosis and/or therapy, including a detection device for detection of the presence of an object in the vicinity of a movable part of the apparatus, which detection device comprises:

a signal source for producing an electric signal, a transmitter unit which is connected to the signal source in order to produce, in the vicinity thereof, an electric field corresponding to the electric signal, a detection unit which is arranged in the vicinity of the transmitter unit in order to detect an electric field in the vicinity thereof, a receiver which is responsive to a control unit and which is arranged to receive on an input an input signal which corresponds to the electric field in the vicinity of the detection unit, and to produce an output signal $V_o$ corresponding to the input signal, and the control unit for automatically adjusting the receiver in order that the output signal $V_o$ of the receiver is adjusted to a predetermined nominal zero value in the absence of motion of the movable part of the apparatus.

2. An apparatus as claimed in claim 1, in which the control unit includes a controllable transfer unit which is arranged for the controllable transfer of the output signal of the signal source to an input of the receiver in order to control the output signal $V_o$ of the receiver to the nominal zero value.

3. An apparatus as claimed in claim 2, in which the control unit includes an adjusting unit which is arranged to control the transfer of the transfer unit in dependence on control unit inputs comprising the output signal $V_o$ of the receiver.

4. An apparatus as claimed in claim 1, in which the detection device for electromagnetic detection is constructed as a device for capacitive detection, in which the transmitter unit is constructed as a source electrode for producing in its vicinity an electric field which corresponds to the electric signal, and in which the detection unit is constructed as a detection electrode for the detection of the electric field in its vicinity.

5. An apparatus as claimed in claim 4, in which the detection electrode is virtually grounded.

6. An apparatus as claimed in claim 5, in which virtual grounding is realized in that the detection electrode is connected to a first input of an operational amplifier which is connected to the output via a feedback chain, a second input of said amplifier being grounded.

7. An apparatus as claimed in claim 2, in which the detection device for electromagnetic detection is constructed as a device for capacitive detection, in which the transmitter unit is constructed as a source electrode for producing in its vicinity an electric field which corresponds to the electric signal, and in which the detection unit is constructed as a detection electrode for the detection of the electric field in its vicinity.

8. An apparatus as claimed in claim 3, in which the detection device for electromagnetic detection is constructed as a device for capacitive detection, in which the transmitter unit is constructed as a source electrode for producing in its vicinity an electric field which corresponds to the electric signal, and in which the detection unit is constructed as a detection electrode for the detection of the electric field in its vicinity.

9. An apparatus as claimed in claim 7, in which the detection electrode is virtually grounded.

10. An apparatus as claimed in claim 8, in which the detection electrode is virtually grounded.

11. An apparatus as claimed in claim 9, in which virtual grounding is realized in that the detection electrode is connected to a first input of an operational amplifier which is connected to the output via a feedback chain, a second input of said amplifier being grounded.

12. An apparatus as claimed in claim 10, in which virtual grounding is realized in that the detection electrode is connected to a first input of an operational amplifier which is connected to the output via a feedback chain, a second input of said amplifier being grounded.

13. An apparatus as claimed in claim 1 wherein the control unit is responsive for selecting either a fast or a slow adjustment of the output signal $V_o$ to the predetermined nominal value.

14. An apparatus as claimed in claim 1 wherein the control unit is responsive for providing adjustment of the output signal $V_o$ to the predetermined nominal value in the absence of motion of the moveable part and for preventing adjustment of the output signal $V_o$ to the predetermined nominal value in the presence of motion of the moveable part.

15. An apparatus as claimed in claim 3 wherein the control unit inputs further comprise a select signal for selecting either a fast or a slow adjustment of the output signal $V_o$ to the predetermined nominal value in the absence of motion of the moveable part.

16. An apparatus as claimed in claim 3 wherein the control unit inputs further comprise an enable signal for providing adjustment of the output signal $V_o$ to the predetermined nominal value in the absence of motion of the moveable part.

17. An apparatus for medical diagnosis and/or therapy, including a detection device for detection of the presence of an object in the vicinity of a movable part of the apparatus, which detection device comprises:

a signal source for producing an electric signal, a transmitter unit which is connected to the signal source in order to produce, in the vicinity thereof, an electric field corresponding to the electric signal, a detection unit which is arranged in the vicinity of the transmitter unit in order to detect an electric field in the vicinity thereof, a receiver which is responsive to a control unit and which is arranged to receive on an input an input signal which corresponds to the electric field in the vicinity of the detection unit, and to produce an output signal $V_o$ corresponding to the input signal, and the control unit for automatically adjusting the receiver in order that the output signal $V_o$ of the receiver is adjusted to a predetermined nominal zero value in the absence of an obstacle to be detected in the vicinity of the movable part of the apparatus.

* * * * *